(12) United States Patent
Kunimoto

(10) Patent No.: US 9,700,687 B2
(45) Date of Patent: Jul. 11, 2017

(54) MEDICINE INHALER AND MEDICINE SUPPLY METHOD

(75) Inventor: Katsushi Kunimoto, Nagoya (JP)

(73) Assignee: Public University Corporation Nagoya City University (JP)

( * ) Notice: Subject to any disclaimer, the term of this patent is extended or adjusted under 35 U.S.C. 154(b) by 1177 days.

(21) Appl. No.: 13/806,389

(22) PCT Filed: Jun. 23, 2011

(86) PCT No.: PCT/JP2011/064341
§ 371 (c)(1),
(2), (4) Date: Dec. 21, 2012

(87) PCT Pub. No.: WO2011/162316
PCT Pub. Date: Dec. 29, 2011

(65) Prior Publication Data
US 2013/0092162 A1 Apr. 18, 2013

(30) Foreign Application Priority Data

Jun. 24, 2010 (JP) ................................. 2010-143776

(51) Int. Cl.
*A61M 15/00* (2006.01)

(52) U.S. Cl.
CPC .... *A61M 15/0028* (2013.01); *A61M 15/0026* (2014.02); *A61M 15/0031* (2014.02);
(Continued)

(58) Field of Classification Search
CPC .. A61M 11/00; A61M 11/002; A61M 11/006; A61M 11/007; A61M 15/00;
(Continued)

(56) References Cited

U.S. PATENT DOCUMENTS

| | | | | |
|---|---|---|---|---|
| 5,178,138 A | * | 1/1993 | Walstrom | A61M 15/0086 128/200.14 |
| 5,724,986 A | * | 3/1998 | Jones, Jr. | A61B 5/087 128/200.14 |
| 5,746,197 A | * | 5/1998 | Williams | A61M 15/0021 128/200.23 |

(Continued)

FOREIGN PATENT DOCUMENTS

| | | |
|---|---|---|
| JP | 2003-038646 A | 2/2003 |
| JP | 2005-510309 A | 4/2005 |
| JP | 2010-501225 A | 1/2010 |

OTHER PUBLICATIONS

English translation of International Search Report for PCT/JP2011/064341.
English translation of International Preliminary Report on Patentability for PCT/JP2011/064341.

*Primary Examiner* — Justine Yu
*Assistant Examiner* — Colin W Stuart
(74) *Attorney, Agent, or Firm* — Quarles & Brady LLP; Gavin J. Milczarek-Desai

(57) ABSTRACT

It becomes possible to stably deliver an inhaled particulate medicine to a targeted part for administration while reducing burdens on a patient. When supplying the particulate medicine into a body by an airflow, a multi-layer flow composed of a core airflow (A) and a clad airflow (B) outside the core airflow is used as the airflow. The medicine is dispersed in the core airflow (A) and velocity of the clad airflow (B) is set higher than that of the core airflow (A). The medicine dispersed in the core airflow (A) reaches the targeted part for administration while the medicine is protected by the clad airflow (B) without contacting a larynx and the like. A cross-sectional area of the airflow is set smaller than that of the larynx. The airflow is supplied to an upper side of the larynx.

10 Claims, 9 Drawing Sheets

Figure 1:
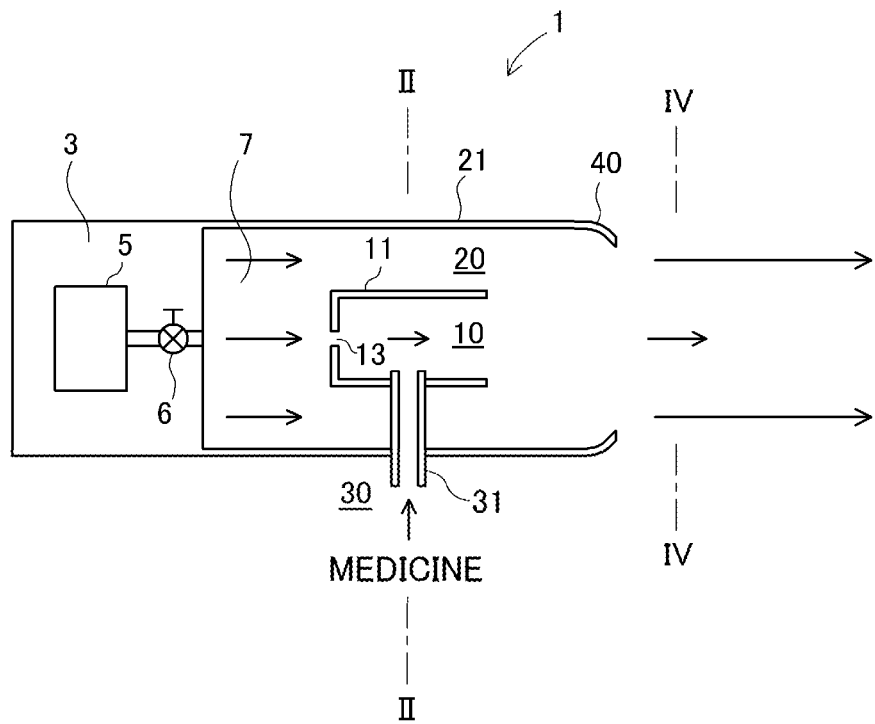
Figure 2:
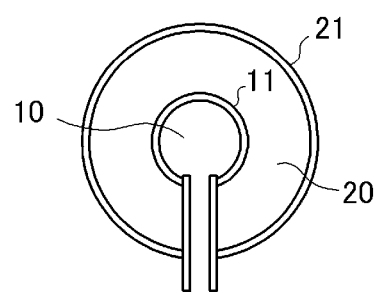
Figure 3:
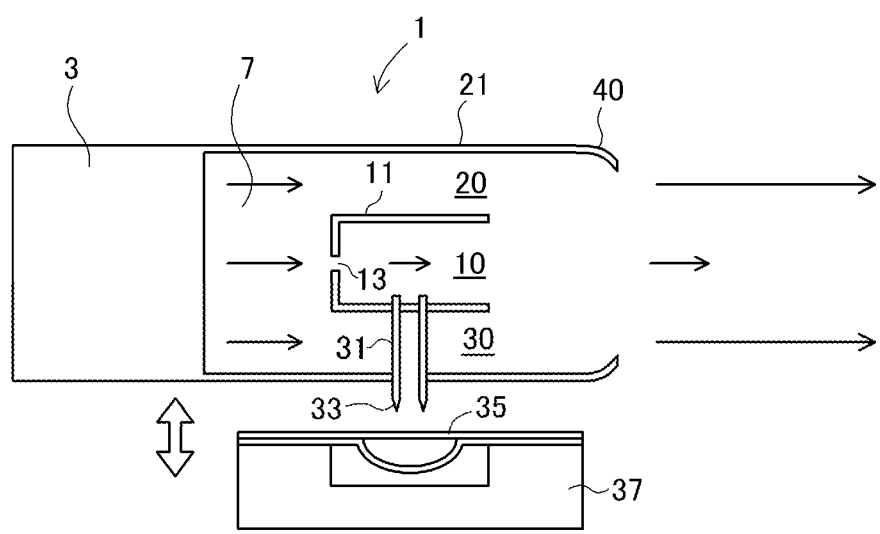

(52) U.S. Cl.
CPC .... *A61M 15/0035* (2014.02); *A61M 15/0045* (2013.01); *A61M 15/0048* (2014.02); *A61M 2202/064* (2013.01); *A61M 2205/073* (2013.01)

(58) Field of Classification Search
CPC .......... A61M 15/0001; A61M 15/0003; A61M 15/002; A61M 15/0021; A61M 15/0023; A61M 15/0028; A61M 15/003; A61M 15/0033; A61M 15/004; A61M 15/0045; A61M 15/0048; A61M 15/0026; A61M 15/009
USPC ............ 128/200.14, 200.19, 200.21, 200.22, 128/203.12, 203.15, 203.21
See application file for complete search history.

(56) References Cited

U.S. PATENT DOCUMENTS

| | | | |
|---|---|---|---|
| 6,752,147 B1* | 6/2004 | Goldemann | A61M 15/0091 128/203.12 |
| 7,464,704 B2* | 12/2008 | Braithwaite | A61M 15/00 128/200.12 |
| 2007/0239058 A1* | 10/2007 | Krasilchikov | A61B 5/087 600/538 |
| 2008/0283439 A1* | 11/2008 | Sullivan | A61M 15/0028 206/531 |
| 2009/0139517 A1* | 6/2009 | Wachtel | A61M 15/0028 128/200.23 |
| 2010/0083963 A1* | 4/2010 | Wharton | A45F 5/00 128/203.15 |
| 2010/0218760 A1 | 9/2010 | Anderson et al. | |

* cited by examiner (I)

(II)

4.0 seconds after inflow    5.0 seconds after inflow

Volume fraction distribution of particles
60L/min 4.0 seconds after completion of inflow Volume fraction distribution of particles
60L/min (A) STATE IN USE (B) HOUSED STATE

MEDICINE INHALER AND MEDICINE SUPPLY METHOD

TECHNICAL FIELD

The present invention relates to improvement of a medicine inhaler that supplies a particulate medicine into a body by an airflow.

BACKGROUND ART

As a method for administering a medicine to a patient suffering from a respiratory disease, there is an inhaler for supplying a particulate medicine into a body using an airflow. For example, an inhaler called nebulizer atomizes a liquid medicine and sprays liquid droplets of the medicine, whereby a patient inhales the liquid droplets orally.

Zanamivir as an anti-flu medicine is also inhaled orally in the form of powders.

If a lung is a targeted part for administration of such the particulate medicine (in the form of powder or liquid droplets (mists)), it is inevitable that the particulate medicine adheres to a larynx or a bronchus when the particulate medicine passes through the larynx or the bronchus. As a result, efficiency of administration of the medicine becomes unstable.

Therefore, conventionally, there have been performed various studies for surely delivering the medicine to the targeted part. For example, an invention described in Patent document 1 reduces a diameter of a tube inserted into a living body such that the tube can be inserted to a point as close as possible to the part for administration, thereby stabilizing the medicine administration.

PRIOR TECHNICAL DOCUMENT

Patent Document

[Patent document 1] JP-A-2003-038646

DISCLOSURE OF THE INVENTION

Problems to be Solved by the Invention

It is true that the medicine administration can be stabilized and efficiency can be improved if the tube can be inserted to the proximity of the administration part. However, insertion of the tube is a burden for the patient.

Therefore, the inventor of the present invention studied to stably deliver the inhaled particulate medicine to the targeted part for administration without inserting any tube, that is, while reducing the burdens on the patient.

Means for Solving the Problem

It is an object of the present invention to solve the above-mentioned problems. A first aspect of the present invention is defined as follows.

A medicine inhaler that supplies a particulate medicine into a body by an airflow, comprising:

a first airflow forming section that forms a core airflow;

a second airflow forming section that forms a clad airflow outside the core airflow, the clad airflow having higher flow velocity than the core airflow;

a medicine supply section that supplies the medicine into the core airflow to disperse the medicine into the core airflow; and an introduction section that introduces the core airflow, in which the medicine is dispersed, and the clad airflow into the body.

The thus-constructed medicine inhaler uses the airflow having the multi-layer structure composed of the core airflow and the clad airflow. Therefore, the clad airflow functions as a tube to inhibit the medicine dispersed in the core airflow from adhering to the larynx or the bronchus, thereby bringing the medicine in the core airflow to a targeted part for administration.

Thus, the particulate medicine can be supplied to the targeted part for administration surely and stably.

The particulate medicine includes a powder medicine and a liquid droplet (mist) medicine.

A cross-sectional shape of the core airflow is not limited specifically, but a circular or elliptical shape is preferable. The clad airflow surrounds the entire circumference of the core airflow. A circular or elliptical shape is preferable also as a cross-sectional shape of an outer periphery of the clad airflow. The core airflow and the clad airflow should preferably have outer peripheral shapes similar to each other (elliptical shape in embodiments described after). Moreover, the core airflow and the clad airflow should preferably share a common axis. In other words, the thickness of the clad airflow surrounding the core airflow should be preferably even. Thus, even if the airflow (core airflow+clad airflow) interferes with obstacles such as vocal cords and the clad airflow is disturbed, the core airflow can be prevented from leaking therefrom and the medicine in the core airflow can be prevented from adhering to the vocal cords and the like.

By providing a difference between the flow velocity of the core airflow and the flow velocity of the clad airflow, the both airflows maintain a separated state. In order to surely prevent contact between the core airflow and organs inside the body, the flow velocity of the clad airflow should be preferably higher than the flow velocity of the core airflow. According to the study by the inventor of the present invention, it is preferable that the velocity of the former airflow is approximately three to a hundred times higher, or further preferably, ten to thirty times higher, than the velocity of the latter airflow.

Cross-sectional shapes, cross-sectional areas and flow velocities of the core airflow and the clad airflow may be adjusted suitably in accordance with the type of the medicine, the targeted part for administration, conditions of the patient and the like.

Further, by adding a turning motion to the clad airflow, the clad airflow (and eventually, the inner core airflow) can be delivered to a deeper part in the body.

The particulate medicine is supplied into the core airflow and is dispersed there. The particulate medicine is delivered exclusively by the core airflow. The dispersing method is not limited specifically. In the case of the liquid droplet medicine, a nozzle may be arranged in the core airflow and the liquid medicine may be forcibly sprayed from the nozzle. Alternatively, a high frequency oscillator may be arranged in the core airflow, and the liquid medicine may be supplied to the oscillator.

Also in the case of the powder medicine, the powder medicine may be forcibly sprayed into the core airflow through a nozzle likewise. Alternatively, depending on the specific gravity of the medicine, the powder medicine may be suctioned up (stirred up) by negative pressure generated by the core airflow and the medicine may be dispersed into the core airflow.

An amount of the medicine introduced into the core airflow can be adjusted by an arbitrary method. In the case where the medicine is forcibly introduced through the nozzle, for example, the introduction amount can be controlled by controlling on and off of a power supply for the introduction. In the case where the medicine is suctioned up by the negative pressure of the core airflow, for example, a shutter may be provided to a medicine introduction hole, and the introduction amount may be controlled by opening and closing the shutter. Alternatively, only a predetermined amount of the medicine may be supplied to the medicine introduction hole. More specifically, a medicine pack (blister pack or the like) encapsulating a predetermined amount of the medicine may be arranged to face a medicine slot.

The core airflow and the clad airflow are formed by an arbitrary airflow generator.

Separate airflow generators for the core airflow and for the clad airflow may be provided respectively. For simplifying the device, an airflow generated by a single airflow generator should be preferably divided into the core airflow and the clad airflow.

A compressed air should be preferably used as an air supply of the airflow generator. It is because a fast airflow is necessary instantly when delivering the air (i.e., the medicine) deeply into the lungs. That is, a compressed air tank and a valve may be prepared, and the compressed air in the tank may be released instantly by adjusting opening and closing of the valve.

A method for filling the tank with the compressed air is not limited specifically. An electric pump may be used or the air may be compressed manually and filled into the tank. Alternatively, a cylinder filled with a compressed air beforehand may be used. In the embodiment described later, the air is compressed in accordance with opening and closing of an introduction section.

BRIEF DESCRIPTION OF THE DRAWINGS

FIG. 1 is a schematic diagram showing a construction of a medicine inhaler according to an embodiment of the present invention.

FIG. 2 is a cross-sectional view taken along the line II-II in FIG. 1.

FIG. 3 is a schematic diagram showing a construction of a medicine inhaler according to another embodiment.

FIG. 4I is a cross-sectional view taken along the line Iv-Iv in FIG. 1 and shows a core airflow A and a clad airflow B.

FIG. 4II is a schematic diagram showing a medicine inhaler airstream that is made smaller than an area of a human larynx C (opening section of bronchus) and the airstream is supplied eccentrically to an upper portion of the larynx C.

FIG. 5 is a simulation result showing a distribution state of a medicine in the case where the medicine inhaler according to the present invention is used.

FIG. 6 is a simulation result showing a distribution state of a medicine in the case where a single layer airflow is used.

FIG. 7 is a view showing an appearance of a medicine inhaler according to a working embodiment. FIG. 7(A) is a view showing a protruded state of a nozzle section, and FIG. 7(B) is a view showing a housed state of the nozzle section.

FIG. 8 is an exploded view showing a construction of a housing section.

FIG. 9 is a cross-sectional view showing a construction of a pump section.

FIG. 10 is a cross-sectional view showing a construction of an airflow forming section.

FIG. 11 is an exploded view showing a construction of a medicine storage section 90.

MODES FOR IMPLEMENTING THE INVENTION

Hereinafter, an embodiment of the present invention will be explained in more details.

FIG. 1 is a conceptual diagram showing a construction of a medicine inhaler 1 according to the embodiment of the present invention.

The medicine inhaler 1 has a blower section 3, a first airflow forming section 10, a second airflow forming section 20, a medicine supply section 30 and an introduction section 40.

For example, the blower section 3 has a compressed air tank 5 and a valve 6. By opening the valve 6, the blower section 3 discharges an air in the tank 5. The air discharged from the blower section 3 passes through a common passageway 7 and flows through the first airflow forming section 10 and the second airflow forming section 20.

The first and second airflow forming sections 10, 20 are defined by an inner pipe 11 and an outer pipe 21. The inner pipe 11 is arranged such that its axis coincides with an axis of the outer pipe 21. Cross-sectional shapes of the inner pipe 11 and the outer pipe 21 may be designed arbitrarily but in order to reduce resistance against the airflows, it is preferable that the inner pipe 11 and the outer pipe 21 have round cross-sectional shapes as shown in FIG. 2.

An inside space of the inner pipe 11 (inside flow passageway) serves as the first airflow forming section 10. The inner pipe 11 has an orifice 13 on a side facing the blower section 3. The orifice 13 serves as resistance against the airflow from the common passageway 7 and reduces velocity of the airflow in the first airflow forming section 10.

A space between the inner pipe 11 and the outer pipe 21 serves as the second airflow forming section 20. In the second airflow forming section 20, resistance against the airflow from the common passageway 7 is small, so velocity of the airflow from the blower section 3 is substantially maintained.

The medicine supply section 30 has a medicine supply pipe 31 penetrating through the inner pipe 11 and the outer pipe 21. The medicine can be supplied from the outside of the outer pipe 21 to the inside of the inner pipe 11 via the medicine supply pipe 31.

In another example shown in FIG. 3, a cutting blade 33 is provided to an outer end of the medicine supply pipe 31. By putting a medicine pack (blister package or the like) 35 close to the cutting blade 33 and pressing the medicine pack 35 against the cutting blade 33, the medicine pack 35 is broken and the inside of the medicine pack 35 communicates with the inside of the inner pipe 11. Since the airflow exists in the inner pipe 11, negative pressure arises in the inner pipe 11 as compared to the inside of the medicine pack 35. Accordingly, the medicine in the medicine pack 35 is suctioned to the inside of the inner pipe 11 and is dispersed into the airflow.

The same components in FIG. 3 as those in FIG. 1 are denoted with the same signs and explanation thereof is omitted. Reference numeral 37 is a medicine supply section that holds a disc of the medicine pack 35 and presses the disc against the cutting blade 33.

A first airflow (core airflow) formed in the first airflow forming section 10 and a second airflow (clad airflow) formed in the second airflow forming section 20 have different flow velocities. Therefore, the first and second airflows do not mix but form a laminar flow. More specifically, the first airflow is defined by an inner diameter space of the inner pipe 11 and the second airflow is defined by an outer diameter of the inner pipe 11 and an inner diameter of the outer pipe 21.

In this example, an outlet portion of the outer pipe 21 (introduction section 40) is narrowed into an elliptical shape in accordance with the shape of a human throat. Therefore, an entirety of the airflow discharged from the outlet portion is deformed into an elliptical shape as shown in FIG. 4(I). In FIG. 4(I), sign A denotes the core airflow formed in the first airflow forming section, and sign B denotes the clad airflow formed in the second airflow forming section.

Figure 4:
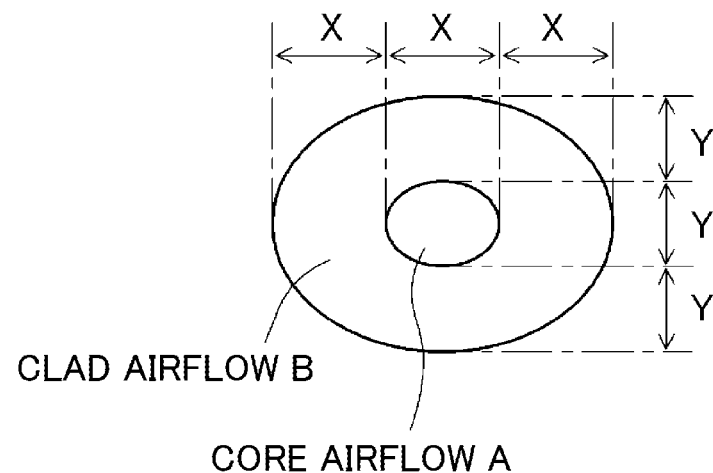
Figure 4:
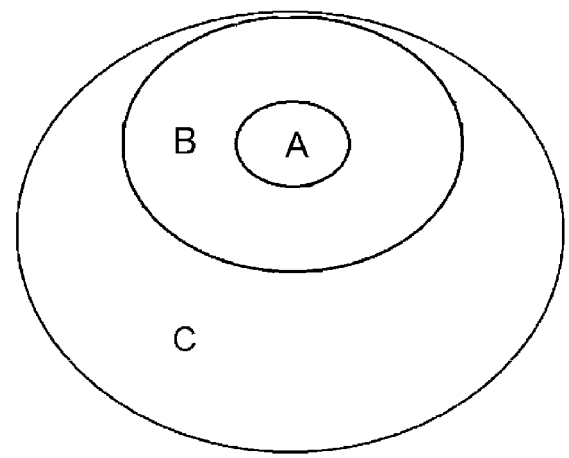
Figure 5:
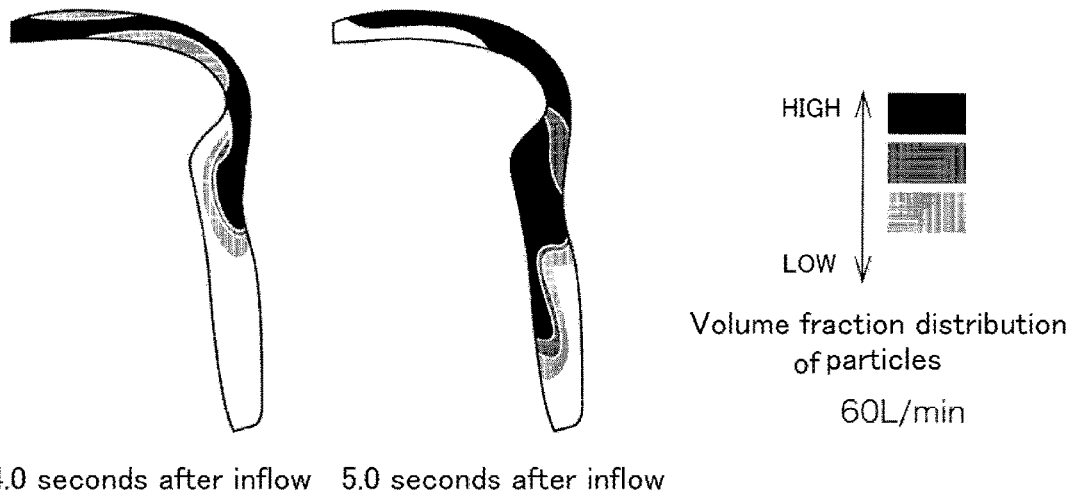
Figure 6:
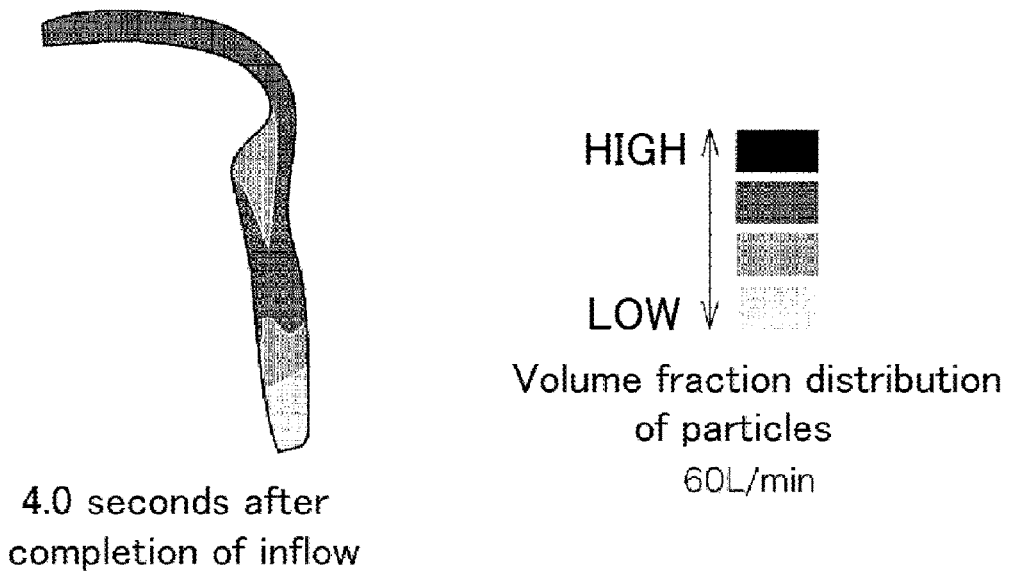

As shown in FIG. 4(II), it is preferable that a cross-sectional area of the airflow is made smaller than an area of a human larynx C (opening section of bronchus) and the airflow is supplied eccentrically to an upper portion of the larynx C. Thus, the particulate medicine contained in the first airflow A can be supplied to the inside of the bronchus more efficiently. The medicine tends to drop due to its weight. Therefore, by supplying the airflow to the upper side of the larynx C first, a margin for the drop can be obtained. In order to supply the airflow eccentrically, it is preferable that an airflow outlet of the nozzle inserted into the mouth faces an upper wall of the larynx C.

In the airflow having the cross-sectional shape shown in FIG. 4 (cross-sectional area=7.2 $cm^2$), it is assumed that the flow velocity of the core airflow A is 3.3 L/m, and the flow velocity of the clad airflow B is 60.0 L/m. Also, it is assumed that 2.4 mg of a powder medicine having a diameter of 3 μm and specific weight of 1.2 $g/cm^3$ is completely dispersed in the airflow A and is administered to a human via a mouth. On that assumption, an existing position of the medicine was simulated (refer to FIG. 5).

The simulation was performed as follows. That is, an inflow boundary is set at a leading end, at which a mouth cavity and the inhaler are combined. The air and the particles flow due to pressure difference between a flow inlet and a flow outlet and disappear at an outflow boundary. It is assumed that the disappeared particles reach main bronchi and then flow into farther lobar bronchi and bronchioli. For analysis of the simulation, the PHOENICS (trade mark) by CHAM and the STAR-CCM+ (trade name) by CD-adapco JAPAN were used A simulation result of the existing position of the medicine on the assumption that the medicine is dispersed in a single layer airflow likewise (that is, there is no inner pipe 11, and the outer diameter of the airflow is equal to the outer diameter of the clad airflow, and the flow velocity is 60.0 L/m) is shown in FIG. 6.

From comparison between FIGS. 5 and 6, it is understood that the dispersion of the medicine is suppressed until the medicine reaches the bronchus by forming the airflow in the multi-layer structure as in the present invention. Thus, the medicine can be precluded from being trapped in the mouth cavity or the larynx. Accordingly, the medicine can be supplied to the originally targeted position for administration (in this case, the bronchus) surely and stably.

With the single laminar flow shown in FIG. 6, the medicine is dispersed before the medicine reaches the bronchus.

Working Embodiment

Hereafter, a medicine inhaler 50 according to a working embodiment will be explained.

FIG. 7 is a perspective view showing an appearance of the medicine inhaler 50 according to the working embodiment. FIG. 8 is an exploded perspective view.

The medicine inhaler 50 has a housing section 51, an introduction section 70 and a medicine storage section 90.

The housing section 51 has side plates 52, 53, a back plate 54 and a bottom plate 55. Upper end portions of the side plates 52, 53 of the housing section 51 are formed in semi-circular shapes. A drum-like base section 71 of the introduction section 70 is arranged rotatably between the upper end portions of the side plates 52, 53.

A pump section 60 is arranged inside the housing section 51. A cut portion 73 is formed in a front edge of the drum-like base section 71 to avoid interference with the pump section 60.

The introduction section 70 is a structure, in which a nozzle section 72 protrudes from the base section 71. With rotation of the base section 71, the nozzle section 72 is switched between a protruded state (FIG. 7A) and a housed state (FIG. 7B). A front edge of the housing section 51 is opened for accommodating the nozzle section 72.

The pump section 60 has three cylinder sections arranged in an up-down direction. Two rear cylinder sections 61, 62 serve as air compression sections.

As shown in FIG. 9, plungers 65, 66 are inserted into the compression cylinder sections 61, 62 movably. The plungers 65 66 are moved up and down by operation rods 75, 76 fixed to the section 71 with the rotation of the base section 71. More specifically, the plungers 65, 66 are at bottom dead centers and compress the air in the compression cylinder sections 61, 62 when the nozzle section 72 is protruded as shown in FIG. 9. When the nozzle section 72 is accommodated, the plungers 65, 66 are at top dead centers, and the inside of the compression cylinder sections 61, 62 is not compressed.

Sign 68 denotes a valve for restricting the air in the compression cylinder sections 61, 62 from moving to the introduction cylinder section 63. The valve 68 allows the movement of the air from the introduction cylinder section 63 to the compression cylinder sections 61, 62. When the nozzle section 72 is accommodated, the air is filled into the cylinder sections 61, 62. When the nozzle section 72 is protruded, the plunger sections 65, 66 move and compress the air in the compression cylinder sections 61, 62.

Sign 69 denotes a knockout pin, which is operated from an outside to open the valve 68, thereby releasing the compressed air in the compression cylinder sections 61, 62 to the inside of the introduction cylinder section 63.

Sign 80 denotes an airflow forming section, whose outer pipe 81 is air-tightly inserted into an upper opening section of the introduction cylinder section 63. In the working embodiment, an O-ring is provided to the upper opening section of the cylinder section 63, and the outer pipe 81 is inserted into the O-ring. Thus, the entire compressed air supplied from the compression cylinders 61, 62 is introduced to the outer pipe 81.

FIG. 10 shows an airflow forming section 80 of the working embodiment, which has the same basic construction as FIG. 1. That is, an inner pipe 83 that shares a common axis with the outer pipe 81 and that has an orifice 85 is provided inside the outer pipe 81. The airflow from the introduction cylinder 63 via the orifice 85 becomes a first airflow (core airflow A) in the inner pipe 83. That is, the inside of the inner pipe 83 serves as the first airflow forming section. A space between the inner pipe 83 and the outer pipe 81 serves as the second airflow forming section and forms a second airflow (clad airflow B).

Sign 87 denotes a medicine supply pipe, which protrudes from a side surface of the inner pipe 83 and penetrates through the outer pipe 81. The medicine supply pipe 87 serves also as a retainer for fixing the inner pipe 83 to the outer pipe 81.

Figure 11:
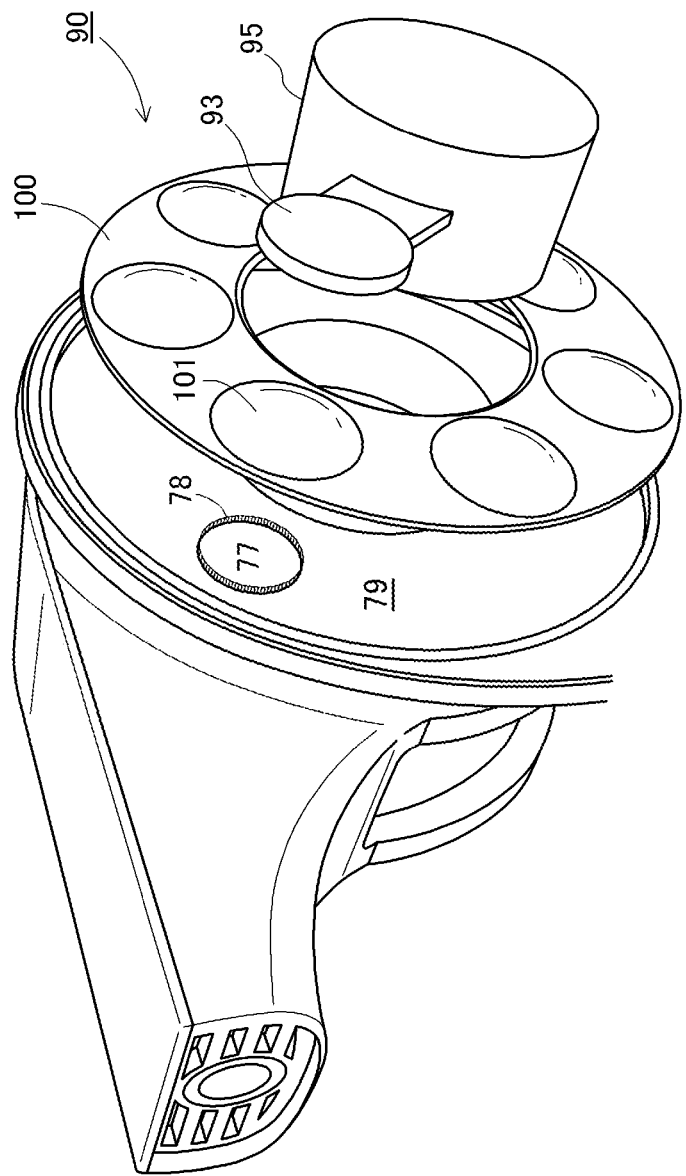

An outer opening section of the medicine supply pipe 87 faces an opening section 77 of a base plate 79 of the base section 71 when the nozzle section 72 is protruded. A cutting blade 78 is formed to stand on a periphery of the opening section 77 (refer to FIG. 11).

The base plate 79 has a disc-like shape and corresponds to a disc-like blister pack 100 for Zanamivir as an anti-flu medicine, for example. The cutting blade 78 faces a blister 101. By pressing the blister 101 toward the base plate 79 with a pressing pad 93, a back of the blister 101 is broken by the cutting blade 78, and the medicine in the blister 101 is released.

The pressing pad 93 protrudes from a rotary shaft 95, which is rotatably inserted to the center of the base section 71. The rotary shaft 95 can move also in an axial direction.

The pressing pad 93, the rotary shaft 95 and a cover member 96 constitute the medicine storage section 90.

The medicine inhaler 50 according to the working embodiment is used as follows.

The cover member 96 of the medicine storage section 90 is detached, and the rotary shaft 95 is also detached. The disc of the blister pack 100 is set such that the disc is pressed against the base plate 79 (refer to FIG. 11).

Figure 7:
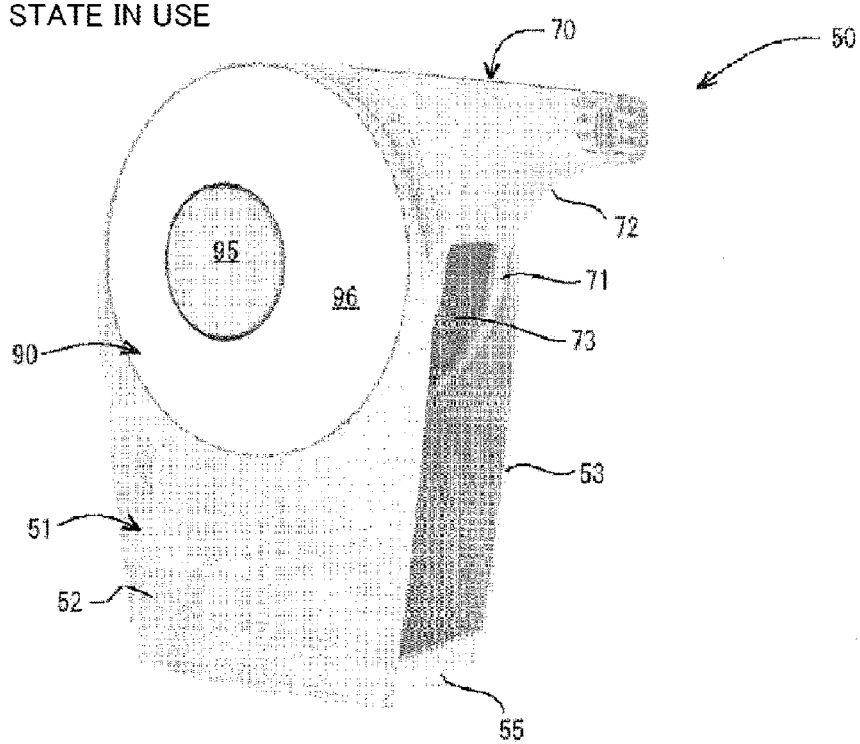
Figure 7:
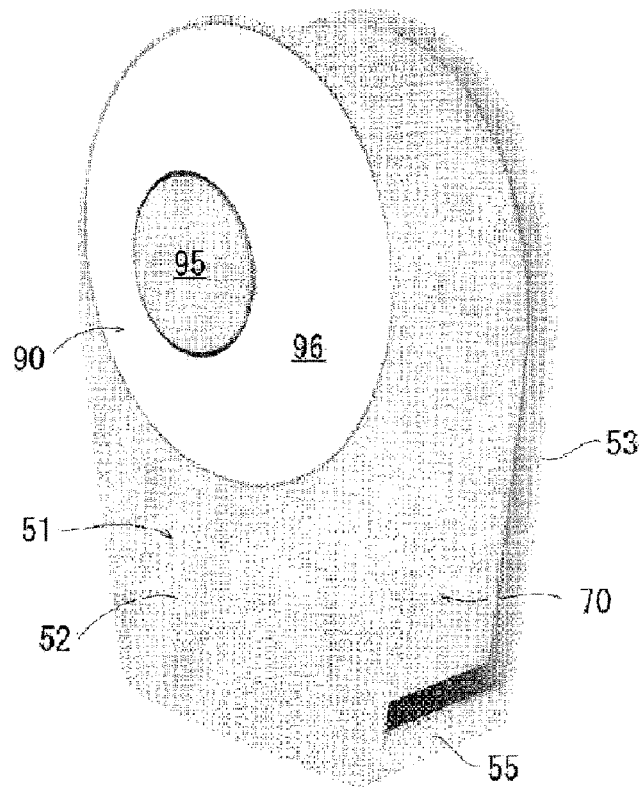
Figure 8:
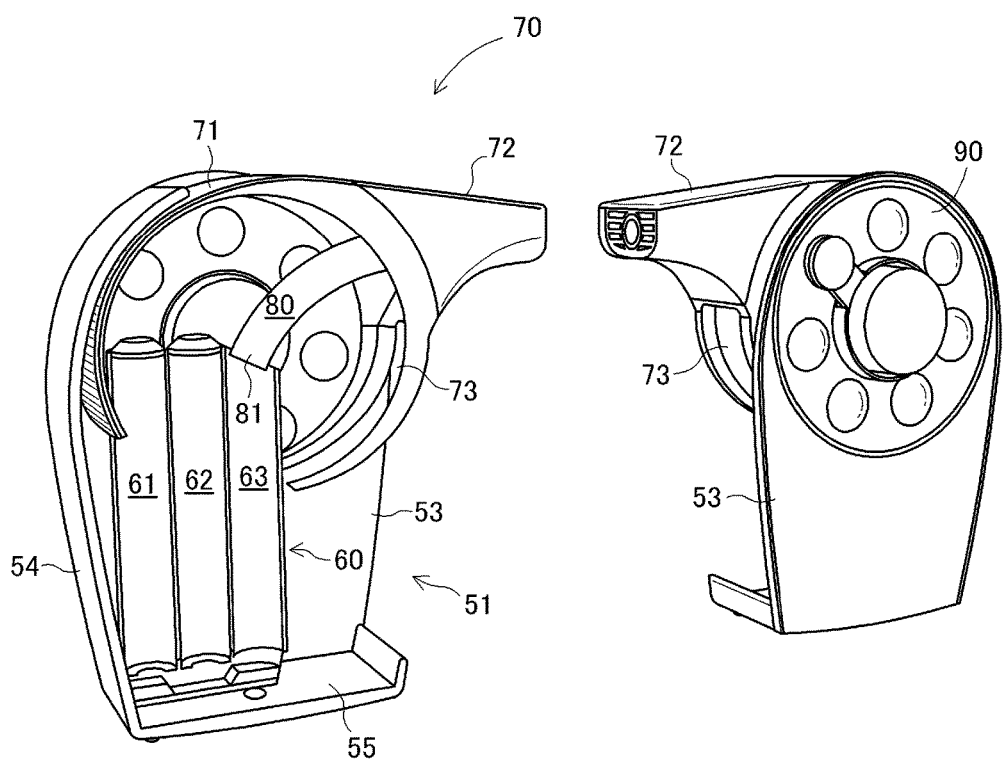
Figure 9:
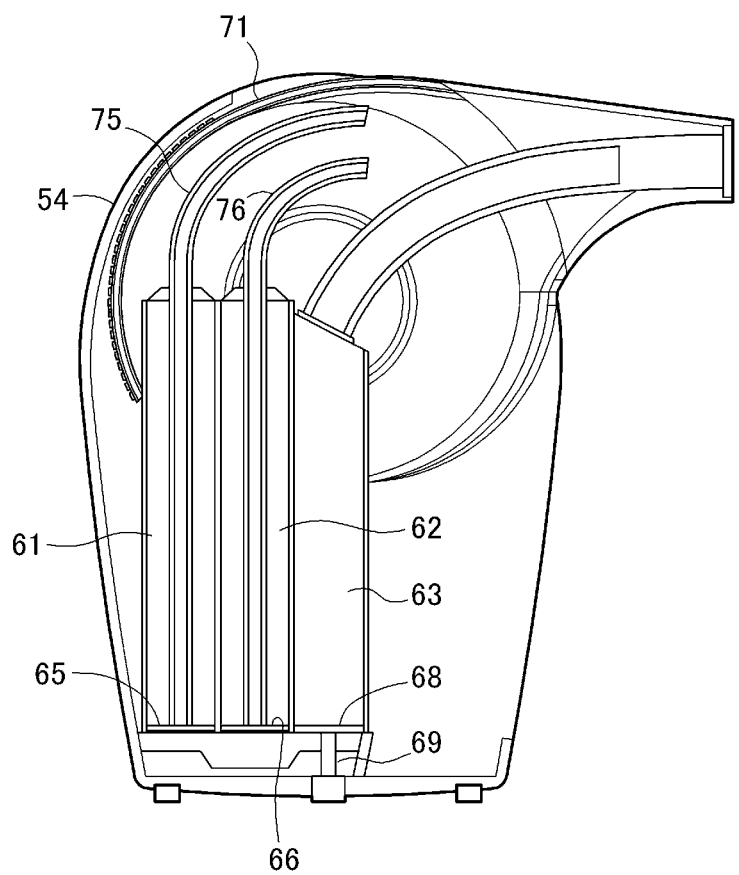
Figure 10:
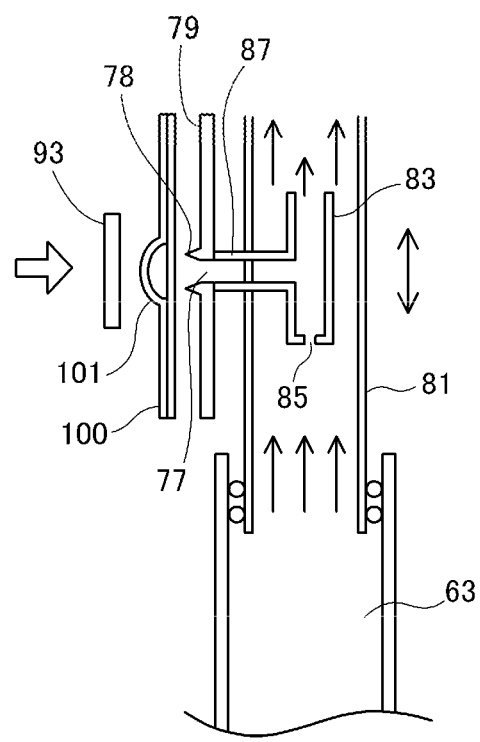

Then, the introduction section 70 is rotated relative to the housing section 51 to bring the nozzle section 72 from the protruded state (FIG. 7A) to the housed state (FIG. 7B). Thus, the plungers 65, 66 in the compression cylinders 61, 62 move from the bottom dead centers to the top dead centers. Accordingly, the air is filled into the compression cylinders 61, 62 through the introduction section 70, the introduction cylinder 63 and the valve 68.

Then, the nozzle section 72 is moved from the housed state (FIG. 7B) to the protruded state (FIG. 7A). At that time, the plungers 65, 66 in the compression cylinders 61, 62 move from the top dead centers to the bottom dead centers, thereby compressing the air in the compression cylinders 61, 62.

At that time, the outer opening section of the medicine supply pipe 87 faces the opening section 77 of the base plate 79. Therefore, if the rotary shaft 95 is pushed in to press the blister 101 against the cutting blade 78 with the pressing pad 93 and to break the back of the blister 101, the inside of the blister 101 and the inside of the inner pipe 83 communicate with each other through the medicine supply pipe 87.

If the release pin 69 is operated to open the valve 68 in this state, the compressed air in the compression cylinders 61, 62 is introduced into the outer pipe 81 and the inner pipe 83 via the introduction cylinder 63. The pressure in the inside space of the inner pipe 83 becomes negative pressure as compared to the pressure in the inside space of the blister 101 due to the air flowing through the inside of the inner pipe 83. Therefore, the medicine in the blister 101 is suctioned up by the airflow (core airflow) in the inner pipe 83 and is dispersed into the same airflow. The clad airflow is formed by the space between the inner pipe 83 and the outer pipe 81.

The flow velocity of the clad airflow is higher than the flow velocity of the core airflow. Therefore, the core airflow and the clad airflow maintain a separated state without mixing with each other and are discharged from the nozzle 72.

With such the multi-layer stream, the clad airflow protects the outer periphery of the core airflow, in which the medicine is dispersed. Therefore, even when the core airflow passes through the mouth cavity or the larynx, the core airflow hardly contacts tissue walls of the mouth cavity or the larynx. Therefore, the medicine can be prevented from adhering to the tissue walls. Thus, the medicine can be delivered to the targeted part for administration surely and stably.

The present invention is not limited to the above explanation of the embodiments and the examples of the invention. Various modifications that can be easily conceived of by a person having ordinary skills in the art without departing from the description of claims are also included in the present invention.

Contents of articles, raid-open patent publications, patent gazettes and the like clearly specified in the specification are incorporated herein by reference.

DESCRIPTION OF REFERENCE NUMERALS 1, 50 Medicine supply device
3 Blower section
10 First airflow forming section
11, 83 Inner pipe
13, 85 Orifice
20 Second airflow forming section
21, 81 Outer pipe
30, 87 Medicine supply pipe
35, 101 Blister of medicine
40, 70 Introduction section
A Core airflow
B Clad airflow

The invention claimed is:

1. A medicine inhaler that supplies a particulate medicine into a body by an airflow, comprising:
    a first airflow forming section that forms a core airflow;
    a second airflow forming section that forms a clad airflow outside the core airflow, the clad airflow having higher flow velocity than the core airflow;
    a medicine supply section that supplies the medicine into the core airflow to disperse the medicine into the core airflow; and
    an introduction section that introduces the core airflow, in which the medicine is dispersed, and the clad airflow into the body,
    further comprising a blower section in a housing for housing the first airflow forming section and the second airflow forming section, wherein a compressed air discharged from the blower section flows through the first airflow forming section and the second airflow forming section to form the core airflow and the clad airflow, respectively; wherein:
    the second airflow forming section has a second airflow passageway communicating with the blower section,
    the first airflow forming section is a first airflow passageway formed inside the second airflow passageway, the first airflow passageway being arranged in the same direction as the second airflow passageway and having an airflow resistance section,
    an air that is blown from the blower section and that is introduced into one end of the first airflow passageway to pass through the first airflow passageway becomes the core airflow;

an air that is blown from the blower section and that is introduced into one end of the second airflow passageway to pass through the second airflow passageway becomes the clad airflow; and the medicine inhaler further has a medicine supply pipe that penetrates through the second airflow passageway to supply the medicine into the first airflow passageway.

2. The medicine inhaler according to claim 1, wherein the core airflow and the clad airflow share a common axis.

3. The medicine inhaler according to claim 1, wherein an outer opening section of the medicine supply pipe that opens outside the second airflow passageway communicates with a medicine pack.

4. The medicine inhaler according to claim 3, wherein the outer opening section has a cutting blade for breaking a medicine pack.

5. The medicine inhaler according to claim 1, wherein the flow velocity of the clad airflow is three to a hundred times higher than the flow velocity of the core airflow.

6. The medicine inhaler according to claim 1, further comprising:
a housing for housing the first airflow forming section and the second airflow forming section, wherein
the housing has a pump section as the blower section,
the introduction section is attached to the housing rotatably such that the introduction section is switchable between a housed state and a protruded state with respect to the housing,
the pump section compresses and stores an air when the introduction section is rotated from the housed state to the protruded state, and
the core airflow and the clad airflow can be formed with the compressed air of the pump section when the introduction section is in the protruded state.

7. The medicine inhaler according to claim 1, wherein
the medicine is supplied from the medicine supply section configured on a side plate of the housing, and
the compressed air is discharged from the blower section configured on a bottom plate of the housing.

8. A medicine supply method for supplying a particulate medicine into a body by an airflow with the medicine inhaler of claim 1, comprising the steps of:
providing the airflow as a multi-layer stream containing a core airflow and a clad airflow outside the core airflow;
dispersing the medicine into the core airflow; and
making flow velocity of the clad airflow higher than flow velocity of the core airflow.

9. The medicine supply method according to claim 8, wherein
the flow velocity of the clad airflow is three to a hundred times higher than the flow velocity of the core airflow.

10. The medicine supply method according to claim 8, wherein
a cross-sectional area of the airflow is smaller than an area of an opening section of a bronchus, and
the airflow is supplied to an upper portion of the opening section of the bronchus.

* * * * *